(12) United States Patent
Vallans et al.

(10) Patent No.: US 6,651,813 B2
(45) Date of Patent: Nov. 25, 2003

(54) WALLET

(75) Inventors: Sidney John Vallans, Derby (GB); Keith Howard Wheatley, Derbyshire (GB)

(73) Assignee: Clearpac Limited, Nottingham (GB)

( * ) Notice: Subject to any disclaimer, the term of this patent is extended or adjusted under 35 U.S.C. 154(b) by 73 days.

(21) Appl. No.: 09/964,783

(22) Filed: Sep. 26, 2001

(65) Prior Publication Data

US 2002/0046962 A1 Apr. 25, 2002

(30) Foreign Application Priority Data

Sep. 27, 2000 (GB) .............................................. 0023624
Mar. 12, 2001 (GB) .............................................. 0106008

(51) Int. Cl.⁷ .............................................. B65D 83/10
(52) U.S. Cl. ...................... 206/366; 206/365; 220/4.23; 220/359.1; 220/839
(58) Field of Search ................................ 206/363–370, 206/63.3, 380, 523, 562–565; 220/4.24, 4.22, 4.23, 837, 839, 359.1, 359.4

(56) References Cited

U.S. PATENT DOCUMENTS

| | | | | |
|---|---|---|---|---|
| 3,394,861 A | * | 7/1968 | Truax | 229/120.07 |
| 3,551,940 A | * | 1/1971 | Edison | 16/225 |
| 3,616,487 A | * | 11/1971 | Dearth | 16/225 |
| 3,629,901 A | * | 12/1971 | Wolf et al. | 16/227 |
| 3,723,061 A | * | 3/1973 | Stahl | 206/370 |
| 4,193,496 A | | 3/1980 | Barratt | |
| 4,784,267 A | * | 11/1988 | Gessler et al. | 206/438 |
| 4,886,165 A | * | 12/1989 | Annett | 206/370 |
| 5,271,892 A | * | 12/1993 | Hanson et al. | 422/25 |
| 5,281,391 A | | 1/1994 | Hanson et al. | |
| 5,938,068 A | * | 8/1999 | Atkins et al. | 220/839 |
| 6,109,515 A | * | 8/2000 | Duboff | 229/125.33 |

FOREIGN PATENT DOCUMENTS

EP            0 242 035       10/1987

* cited by examiner

Primary Examiner—J. Mohandesi
(74) Attorney, Agent, or Firm—Smith-Hill and Bedell

(57) ABSTRACT

A wallet for the safe disposal of sharp implements including a closeable cover member. Implement receiving means is provided on the cover member to receive at least one sharp implement. When one or more sharp implements are received in the receiving means, the cover member can be closed over the receiving means to hold the implements in the wallet. The cover member may comprise first and second portions. At least the first portion may define a recess in which the implement receiving means is arranged. Each of the first and second portions may include inner and outer parts. Each outer part is in the form of a flange which are adapted to engage each other when the cover member is closed. A hinge member may extend outwardly from the cover member. A part of the second portion arranged over the implement receiving means may be formed of a transparent material.

20 Claims, 5 Drawing Sheets

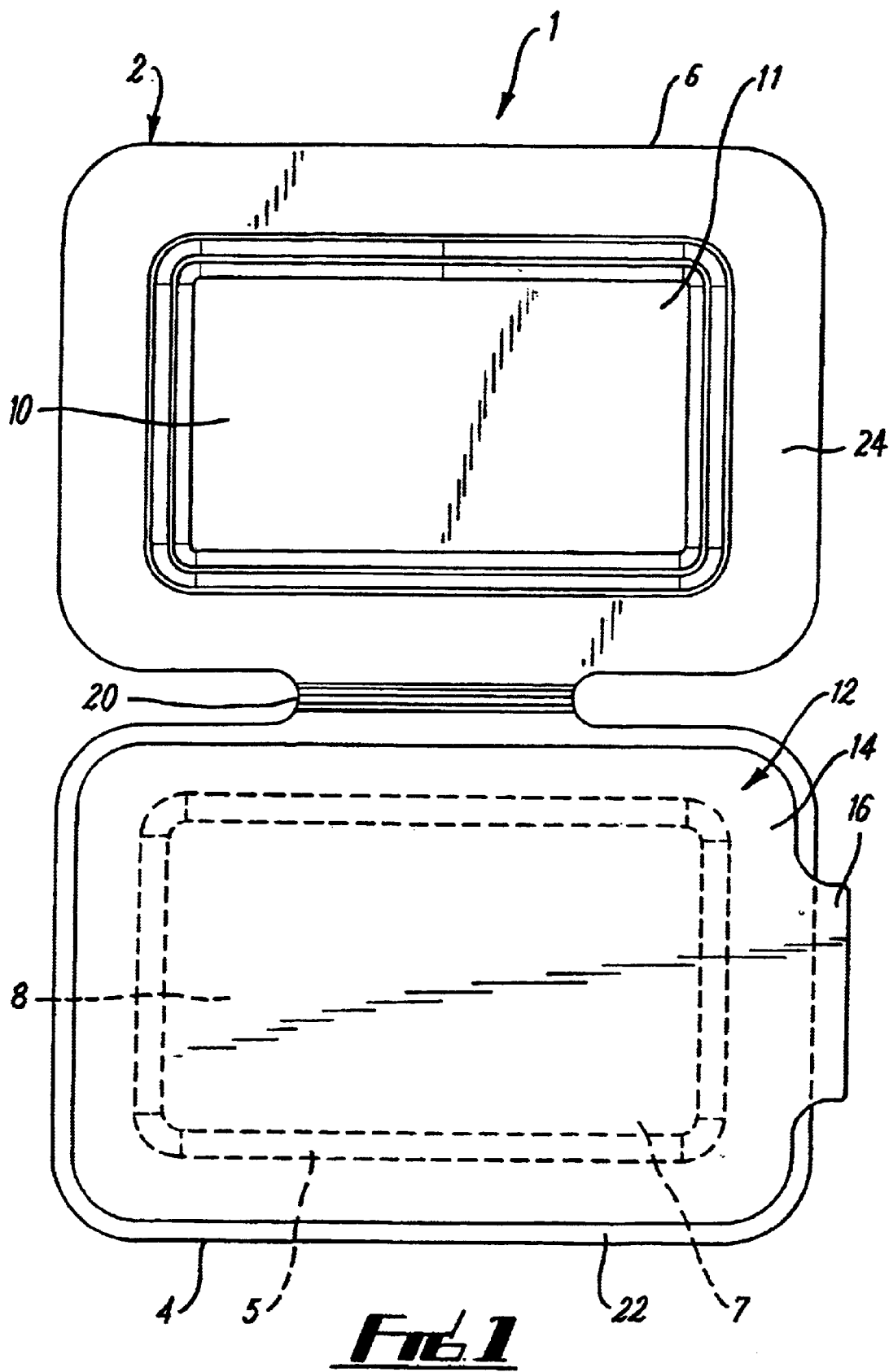

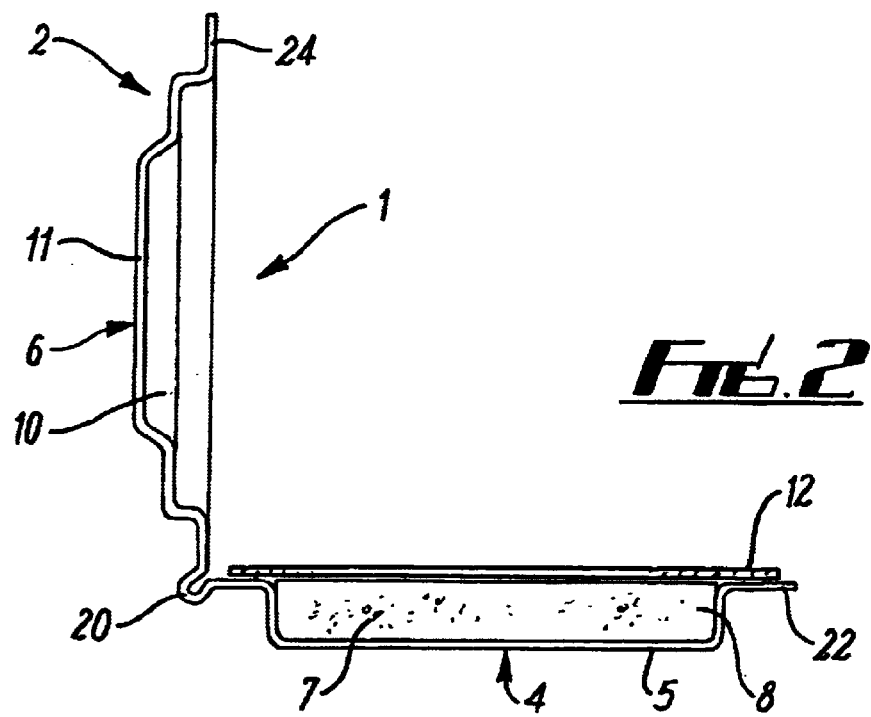
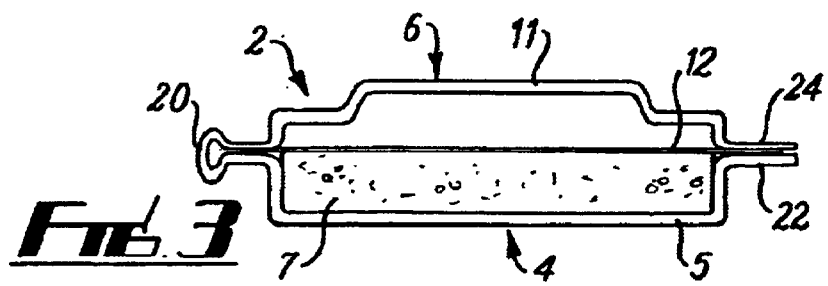
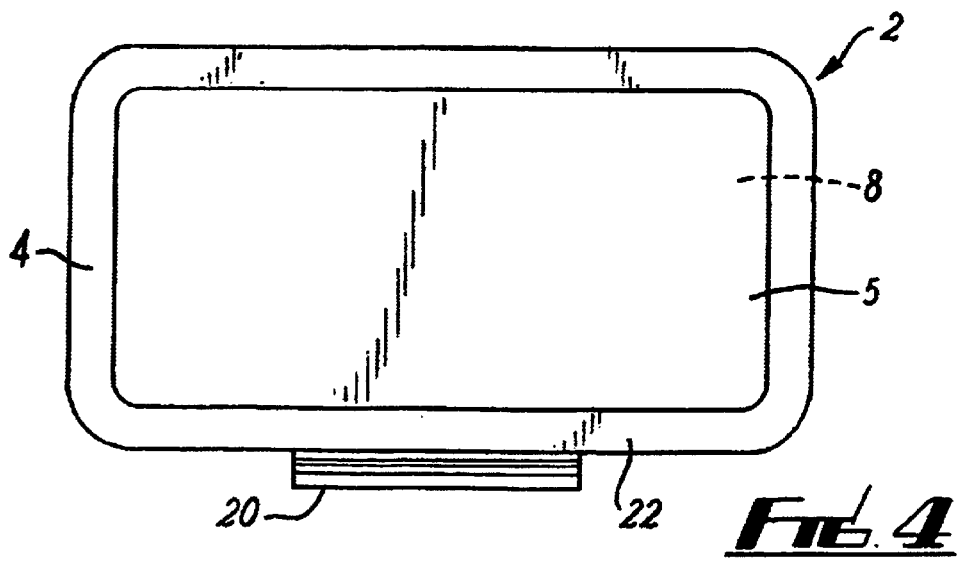

WALLET

FIELD OF THE INVENTION

This invention relates to wallets. More particular but not exclusively to wallets for use in surgical theatres, for the safe disposal of sharp implements. Such wallets are generally known as discard wallets.

BACKGROUND OF THE INVENTION

Current discard wallets comprise A layer of soft resilient material on a backing layer capable of being folded over on itself and having a layer of adhesive along one face. The wallet can be closed to secure any sharp implements within the soft material.

SUMMARY OF THE INVENTION

According to one aspect of the invention there is provided a wallet for the safe disposal of sharp implements, the wallet comprising a closeable cover member, and an implement receiving means on the cover member to receive at least one sharp implement, wherein when one or more sharp implements are received in the receiving means, the cover member can be closed over the receiving means to hold the implements in the wallet.

According to a second aspect of the invention, there is provided a wallet for the safe disposal of a sharp implement, the wallet comprising a closeable cover member, and an implement receiving means on the cover member to receive at least one sharp implement, wherein when at least one sharp implement is received in the receiving means, the cover member can be closed over the receiving means to hold the implement in the wallet, the cover member comprising first and second portions, at least the first portion defining a recess in which the implement receiving means is arranged.

According to a third aspect of the invention, there is provided a wallet for the safe disposal of a sharp implement, the wallet comprising a closeable cover member, and an implement receiving means on the cover member to receive at least one sharp implement, wherein when the sharp implement is received in the receiving means, the rover member can be closed over the receiving means to hold the implement in the wallet, the cover member comprising first and second portions and each portion of the cover member comprising an inner and an outer part, the outer part comprising a flange, and the flange of the first portion being adapted to engage the flange of the second portion when the cover member is in the closed condition.

According to a fourth aspect of the invention, there is provided a wallet for the safe disposal of a sharp implement, the wallet comprising a closeable cover member, and an implement receiving means on the cover member to receive at least one sharp implement, wherein when the sharp implement is received in the receiving means, the cover member can be closed over the receiving means to hold the implements in the wallet, the cover member comprising two portions connected to each other by a hinge member which extends outwardly from the cover member allowing the first portion to be folded relative to the second portion such that they lie substantially in face to face contact with each other in the closed position.

According to a fifth aspect of the invention, there is provided a wallet for the safe disposal of a sharp implement, the wallet comprising a closeable cover member formed of a generally rigid material, and an implement receiving means on the cover member to receive at least one sharp implement, wherein when the sharp implement is received in the receiving means, the cover member can be closed over the receiving means to hold the implements in the wallet.

According to a sixth aspect of the invention, there is provided a wallet for the safe disposal of a sharp implement, the wallet comprising a closeable cover member, and an implement receiving means on the cover member to receive at least one sharp implement, wherein when the sharp implement is received in the receiving means, the cover member can be closed over the receiving means to hold the implements in the wallet, the cover member comprising first and second portions, the implement receiving means being provided on the first portion and a part of the second portion arranged over the implement receiving means when the cover member is in the closed position being formed of a transparent material.

Preferably the cover member comprises first and second portions, each having an inwardly facing surface. At least the first portion may have a recess defined by the surface. The implement receiving means may be arranged in the recess in the first portion. Preferably the second portion defines a recess, the recess in the second portion providing a space for the implements to be received in the implement receiving means.

Preferably, each portion of the cover member comprises an inner part and an outer part, The inner part may define the recess. The outer part may be a flange. Preferably the flange of the first portion can engage the flange of the second portion when the cover member is in the closed condition. Tie flanges of the first and second portions may lie in substantially face to face engagement with each other when the cover member is in the closed position.

Preferably, there is a hinge means between the first and second portions. In one embodiment the hinge means comprises a hinge member which may extend outwardly from the first and second portions to allow the first and second portions to be arranged in said face to face engagement in the closed position.

In another embodiment, the hinge means comprises a region between the first and second portions defining a slit therein. The slit may be curved and may comprise substantially a semi-circle. The slit may have a curved central region and oppositely outwardly extending end regions. The end regions may extend along a line delimiting the first and second portions of the cover member.

In this other embodiment, the hinge means may include a plurality of said slits, conveniently three of said slits, which may extend one after the other along said region. The, or each, slit may be so defined by said region that, when the cover member is closed, the, or each, curved region extends outwardly therefrom, preferably, generally in the plan of the first or second, cover member.

Preferably the cover member is made of a rigid material, which may be a rigid plastics material. Preferably a part of the second portion, which is arranged over the implement receiving means when the cover member is in the closed condition, is transparent. Most preferably, substantially the whole of the cover member made of a transparent material. An example of a suitable plastics material is polyterephthalic diol-ester.

The implement receiving means may be formed of a resilient material which may be a foam material, for example a polyolefine foam, which may be a cross-liked polyolefine foam. The implement receiving means preferably comprises a pad of foam material.

Securing means may be provided to secure the wallet to a support, for example a table or bench. The securing means may comprise adhesive means to enable the wallet to be adhered to the support. The adhesive means may comprise a pressure sensitive adhesive which may be in the form of an adhesive tape, conveniently, a double-sided adhesive tape.

Preferably the first portion of the cover member may have a layer of adhesive covering at least part of its inwardly facing surface. The adhesive may be a pressure sensitive adhesive, which may be provided in the form of a tape, suitably a double sided tape.

A typical adhesive tape suitable for use with the preferred embodiments of this invention comprises a flexible substrate having a first and second faces and an adhesive material applied to the first and second faces. A release member, which may be a flexible sheet to which the adhesive does not permanently adheres may be applied to each respective face.

The wallet may be a discard wallet.

Embodiments of the invention will now be described for the purpose of illustration only, with reference to the accompanying drawings, in which:

BRIEF DESCRIPTION OF THE DRAWINGS

FIG. 1 is a plan view of a wallet according to one embodiment of the invention in an open position.

FIG. 2 is a cross-section through the wallet shown in FIG. 1 in an open position;

FIG. 3 is a cross-section through the wallet shown in FIGS. 1 and 2 in a closed position;

FIG. 4 is a plan view of the wallet shown in FIGS. 1 to 3 in a closed position;

DETAILED DESCRIPTION OF PREFERRED EMBODIMENTS

Figure 5:
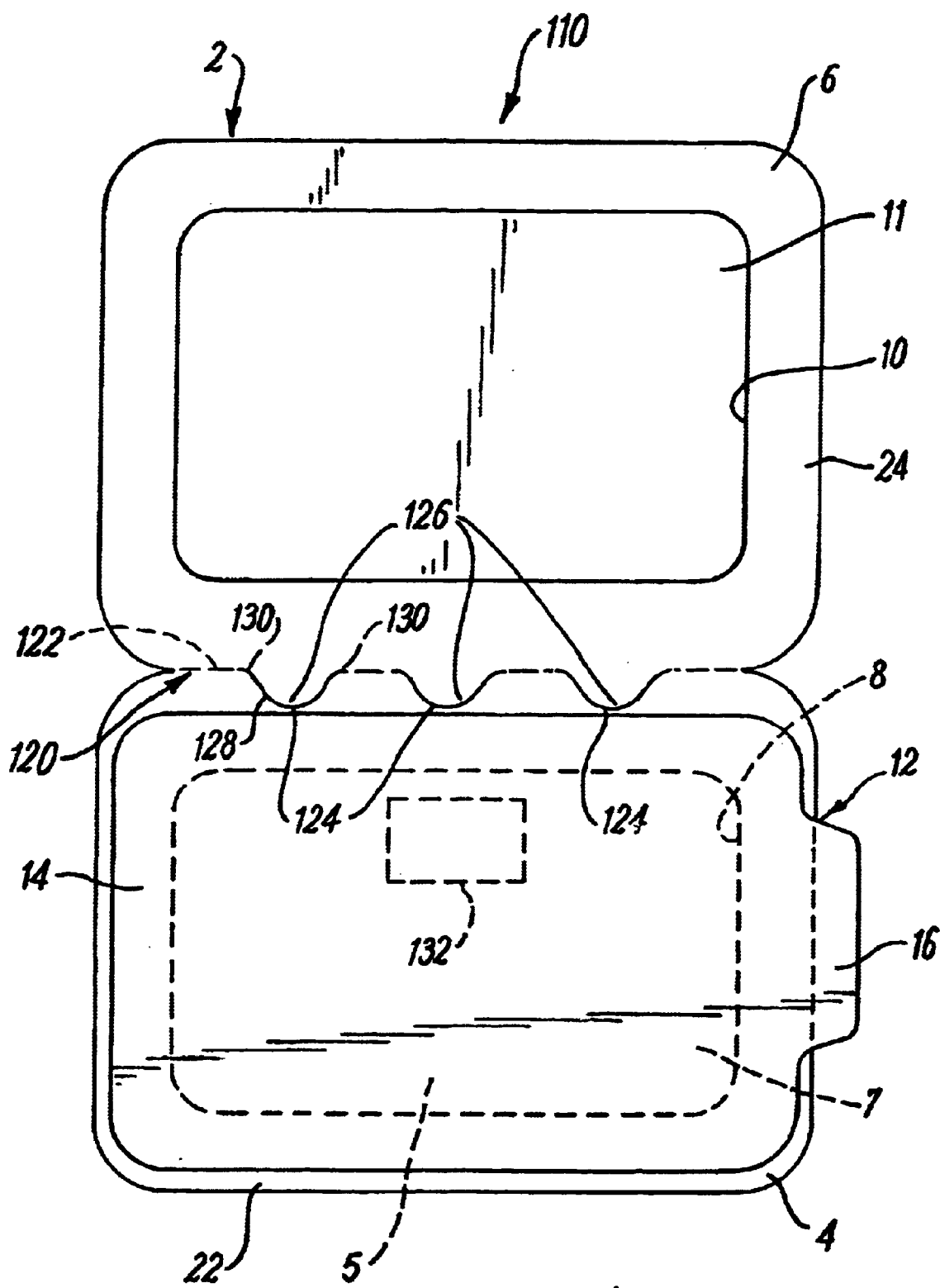
FIG. 5 is a plan view of a further embodiment of a wallet in an open position.

Referring to FIGS. 1 to 4 of the drawings, there is shown a first embodiment of a wallet In the form of a discard wallet generally designated 1 which comprises a cover member 2 moulded from amorphous polyterephthalic diol-ester (P.E.T.P.).

The cover member 2 comprises a first portion 4 having a raised part 5 which defines a recess 8. An implement receiving means in the form of a pad of foam material 7 is held within the recess 8. Surgical implements e.g. needles, scalpel blades etc. can be inserted into the pad of foam material 7 and held in the recess 8 by the pad 7. In this way the sharp implements are prevented from contacting the first portion 4 of the cover member 2 directly.

Adhesive means covers the first portion 4 of the cover member 2 and the pad 7. The cover member 2 also includes a second portion 6 hingedly attached to the first portion 4 at a hinge 20. The adhesive means may be in the form of a tape 12 having adhesive applied to both faces thereof i.e. a double sided adhesive tape. A release layer 14 is provided over the adhesive and includes a tab 16. Before use, the release layer 14 over the adhesive material is peeled away by pulling the tab 16.

A further recess 10 is defined by a raised part 11 on the second portion 6 of the cover member 2. Due to the adhesive layer on the first portion 4, sharp implements will stick to the surface of the first portion 4 and not bounce around loosely in the recess 10 of the second portion 6. The recess 10 of the second portion 6 allows larger numbers of sharp implements to be discarded safely whilst keeping the two flanges 22, 24 in a substantially face to face engagement in a closed position (see FIG. 3).

The portions 4, 6 are linked by a hinge 20 which extends outwardly from the cover member 2. This hinge 20 allows the first and second portions 4 and 6 to be folded relative to each other such that they lie in substantially face to face engagement with each other when the cover member 2 is in a closed position (see FIG. 3). The adhesive tape 12 present on the inwardly facing surface of the first portion 4 seals the wallet 1 closed.

Each portion 4, 6 of the cover member 2 comprises an outer and an inner part. This can be most clearly seen in FIG. 4. The inner part is defined by the recess 8, 10 of the respective portion. The outer part is in the form of a flange 22, 24. The recesses 8, 10 are generally rectangular in shape and the flanges 22, 24 surround the recesses 8, 10. The flanges 22, 24 respectively surround the recesses 8 and 10 of the cover member 2 so that in the process of closing the wallet 1, the user does not need to press down on the material over the recess 8 or 10. This significantly reduces the possibility of a sharp implement being accidentally forced through the cover member 2 of the wallet 1. Instead, it is only necessary for the user to press down on the flanges 22, 24 surrounding the recesses 8, 10 to dose the wallet 1.

Referring to FIGS. 5 to 8, there is shown a further embodiment of a discard wallet generally designated 110. The wallet 110 includes many of the features of the discard wallet 1, shown in FIGS. 1 to 4, and these have been designated with the same reference numeral. These features will not be described in further details.

The embodiment shown in FIGS. 5 to 9 differs from the embodiment shown in FIGS. 1 to 4 by a different binge means, which is generally designated 120. The hinge means 120 comprises a fold line 122 about which the first and second portions 4, 6 can fold relative to each other. The hies means 120 also includes three spaced curved slits 124 circumscribing respective hinge members 126.

Figure 6:
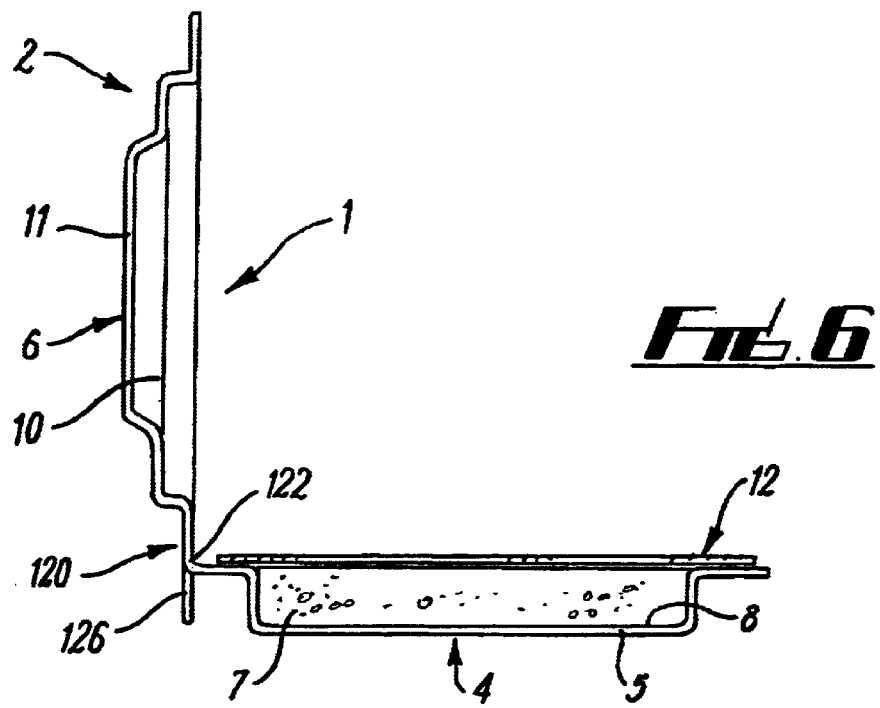
FIG. 6 is a cross-sectional view through the wallet shown in FIG. 5, in an open position.
Figure 7:
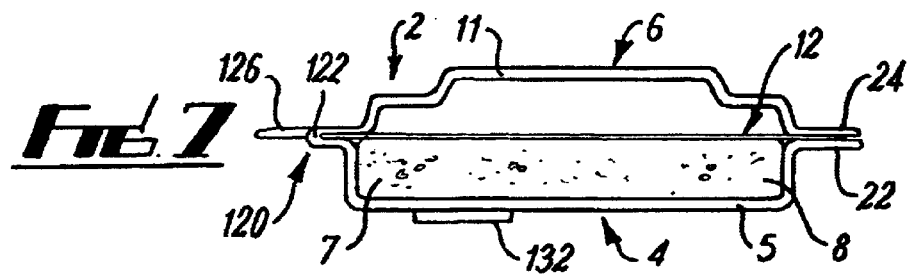
FIG. 7 is a cross-sectional view through the wallet shown in FIGS. 5 and 6, in a closed position.
Figure 8:
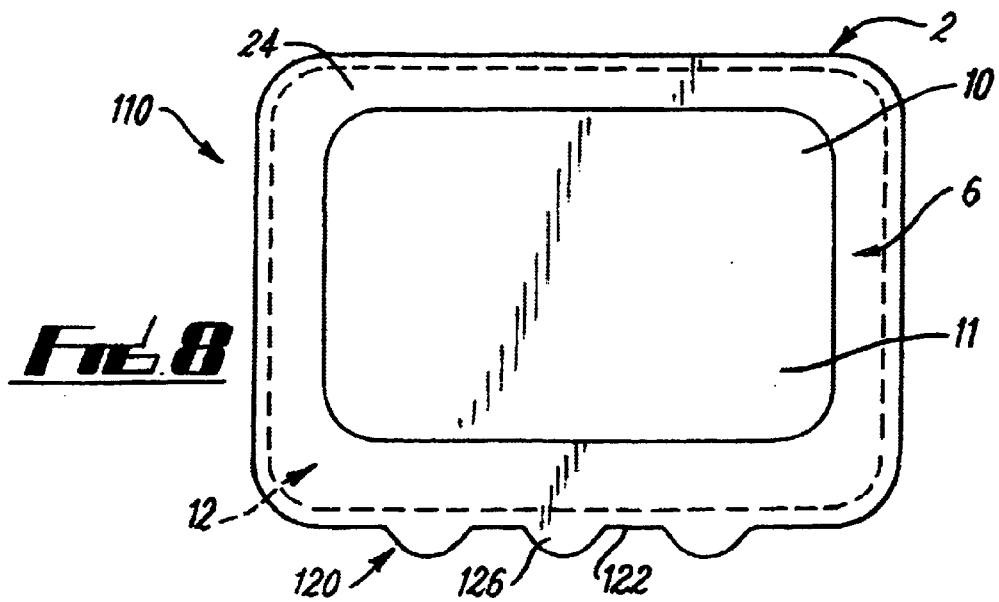
FIG. 8 is a plan view of the wallet shown in FIGS. 5 to 7 in a closed position.

Each curved slit 124 comprises a central carved section 128 and opposite end regions 130. The opposite end regions 130 are collinear with the fold line 122. When the second portion 6 is folded relative to the first portion 4, as shown in FIGS. 6 and 7 to close the wallet 110, the hinge members 126 project rearwardly from the second portion 6, since the hinge members 126 are defined by curved lines, no sharp edges are presented upon which user can cut themselves.

Securing means, in the form of a piece of a double sided adhesive tape 132, is provided to secure the wallet 110 to a suitable support, for example a bench or a table to prevent it from slipping off. This is particularly advantageous when the wallet is used In an ambulance, since the movement of the vehicle could cause the wallet 110 to slide off the support on which it is placed. A similar such securing means can be provided on the wallet shown in FIGS. 1 to 4.

Figure 9:
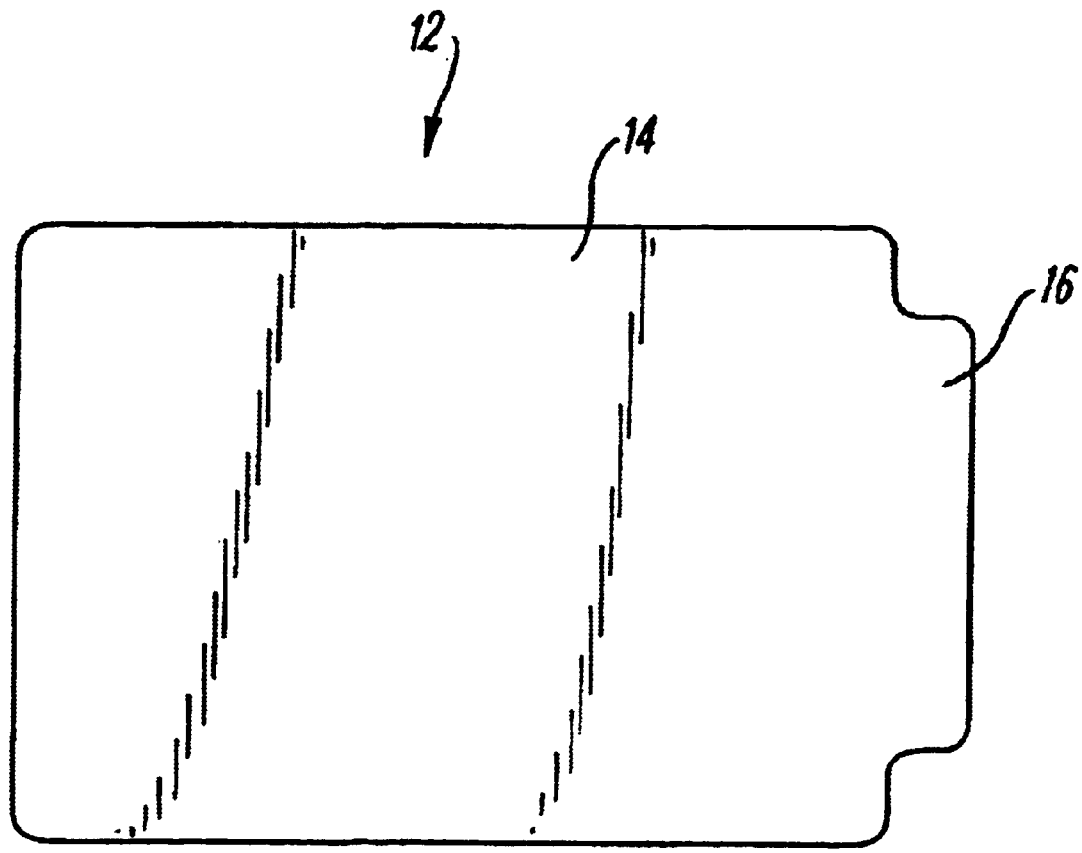
FIG. 9 is a plan view of adhesive means.
Figure 10:
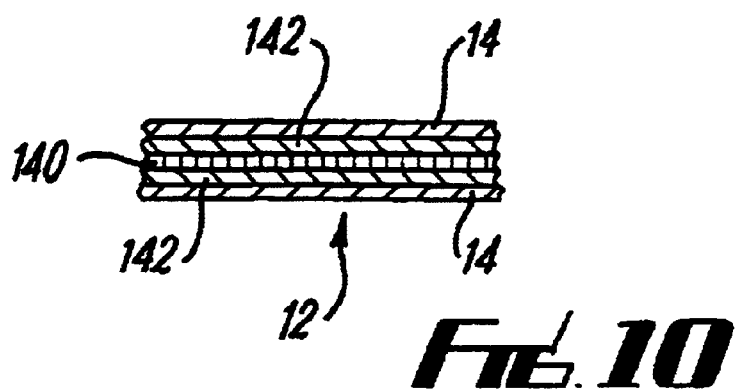
FIG. 10 is a schematic side view of part of the adhesive means shown in FIG. 9.

Referring to FIGS. 9 and 10, there is shown a respective plan and a side view of double-sided adhesive tape 12 which could be used with the embodiments shown in FIGS. 1 to 8.

Referring to FIG. 10, the tape 12 comprises a central substrate 140 upon both faces of which is provided a layer of a pressure sensitive adhesive 142. Respective release sheets 14 are provided on each of the adhesive layers 142 to prevent the adhesive inadvertently sticking to other articles.

In order to apply the tape to the cover member 2, one of the release sheets 14 is peeled off. The tape 12 is then applied such that the uncovered adhesive sticks to the portion 4 of the cover member 2. When this wallet is to be used, the other release sheet 14 is removed by pulling out the tab 16 thereon.

An advantage of the above described embodiments is that they are formed of a transparent material, so that when the wallet 1, or 110 is closed a person using the present discard wallet will know how many sharp implements have been disposed in a particular wallet. Another advantage of the above embodiments of the present invention is that prior discard pads tend to be weakened when they come into contact with water or blood, The use of a rigid plastics material e.g. amorphous P.E.T.P., makes it resistant to sharp implements. This property is not compromised by contact with water or blood in the same way as with prior discard pads.

A further advantage of the preferred embodiments of the present embodiment is that the hinges allows the wallet to be closed securely and is unlikely to open inadvertently. In this way, the risk of contamination or possible loss of contents from the wallet is minimised. A used wallet may be disposed of by incineration.

Various modifications may be made to the above described embodiment without departing from the scope of the invention. For example, there may be a recess provided on only one of the portions 4, 6 of the cover member 2 sufficient to accommodate sharp implements as required.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A wallet for the safe disposal of a sharp implement, the wallet comprising:
    a closeable cover member, comprising first and second portions, each having an inwardly facing surface, at least the first portion having a recess defined by the surface;
    an implement receiving means on the cover member to receive at least one sharp implement, the implement receiving means being arranged in the recess in the first portion; and
    a hinge means provided between the first and second portions, the hinge means comprising a region between the first and second portions defining a slit therein, the slit having a curved central region and oppositely outwardly extending end regions, the end regions extending along a line delimiting the first and second portions of the cover member;
    wherein when one or more sharp implements are received in the receiving means, the cover member can be closed over the receiving means to hold the implements in the wallet.

2. A wallet according to claim 1 wherein the second portion defines a recess, the recess in the second portion providing a space for the implements to be received in the implement receiving means.

3. A wallet according to claim 2 wherein each portion of the cover member comprises an inner part and an outer part, the inner part defining the recess, and the outer part comprising a flange, the flange of the first portion engaging the flange of the second portion when the cover member is in the closed condition.

4. A wallet according to claim 3 wherein the flanges of the first and second portions lie in substantially face to face engagement with each other when the cover member is in the closed position.

5. A wallet according to claim 1 wherein the hinge means comprises a hinge member which extends outwardly from the first and second portions to allow the first and second portions to be arranged in said face to face engagement in the closed position.

6. A wallet according to claim 1 wherein the hinge means includes a plurality of said slits which extend one after the other along said region.

7. A wallet according to claim 1 wherein the slit is so defined by said region that, when the cover member is closed, the curved region extends outwardly therefrom generally in the plane of the first or second cover members.

8. A wallet according to claim 1 wherein the first portion of the cover member has an adhesive covering at least part of its inwardly facing surface.

9. A wallet according to claim 8 wherein the adhesive comprises a pressure sensitive adhesive.

10. A wallet according to claim 9 wherein the pressure sensitive adhesive is provided in the form of a tape.

11. A wallet according to claim 9 wherein the pressure sensitive adhesive is in the form of a double sided tape.

12. A wallet according to claim 1 wherein a part of the second portion, which is arranged over the implement receiving means when the cover member is in the closed condition, is transparent.

13. A wallet according to claim 12 wherein the cover member is made of transparent material.

14. A wallet according to claim 1 wherein the cover member is made of a rigid material.

15. A wallet according to claim 1 wherein the cover member is formed of a polyterephthalic diol-ester.

16. A wallet according to claim 1 wherein the implement receiving means is formed of a resilient material.

17. A wallet according to claim 16 wherein the implement receiving means is in the form of a pad of a foam material.

18. A wallet according to claim 1 including securing means to secure the wallet to a support.

19. A wallet according to claim 18 wherein the securing means comprises adhesive means to enable the wallet to be adhered to the support.

20. A wallet according to claim 19 wherein the adhesive means comprises pressure sensitive adhesive.

* * * * *